United States Patent [19]

Takata et al.

[11] Patent Number: 5,703,124
[45] Date of Patent: Dec. 30, 1997

[54] COMPOSITION CONTAINING ALLYL ISOTHIOCYANATE AND ITS USE

[75] Inventors: Asami Takata; Shoko Numata; Yuichi Mizukami; Yasushi Sekiyama, all of Osaka; Masato Takahashi, Fujinomiya, all of Japan

[73] Assignee: The Green Cross Corporation, Osaka, Japan

[21] Appl. No.: 404,123

[22] Filed: Mar. 14, 1995

Related U.S. Application Data

[63] Continuation of Ser. No. 22,099, Feb. 25, 1993, abandoned.

[30] Foreign Application Priority Data

Feb. 26, 1992 [JP] Japan ................................. 4-076116
May 26, 1992 [JP] Japan ................................. 4-133883
Nov. 2, 1992 [JP] Japan ................................. 4-294578

[51] Int. Cl.$^6$ ........................... A01N 47/40; A01N 47/46
[52] U.S. Cl. ................................... 514/514; 514/515
[58] Field of Search ................................. 514/514, 515

[56] References Cited

U.S. PATENT DOCUMENTS 4,440,783  4/1984  Downing ............................... 514/514
4,702,916  10/1987  Gerio ................................. 514/514

FOREIGN PATENT DOCUMENTS 0427862  4/1990  European Pat. Off. .

OTHER PUBLICATIONS

Chemical Abstracts, vol. 89, No. 11 (1978) 89125c Bodrogi et al.
Chemical Abstracts, vol. 101, No. 9 (1984) 71306.
Chemical Patents Index, Documentation Abstracts Journal Section Ch, Week 9213, AN 099834 (1982).
Kato et al, C.A., vol. 105, (1986) 105:130645m.
Stepanova et al, C.A., vol. 75 (1971) 84393u.

*Primary Examiner*—Allen J. Robinson
*Attorney, Agent, or Firm*—Sughrue, Mion, Zinn, Macpeak & Seas, PLLC

[57] ABSTRACT

An antimicrobial composition comprising AIT and a polyhydric alcohol which may have aldehyde group or ketone group; an antimicrobial composition comprising a surfactant and said composition; a method for treating microorganisms; and a method for retaining freshness of vegetables, etc., both of which methods comprising treating the target substances such as perishables with the composition of the present invention or an aqueous solution containing said composition.

23 Claims, 1 Drawing Sheet

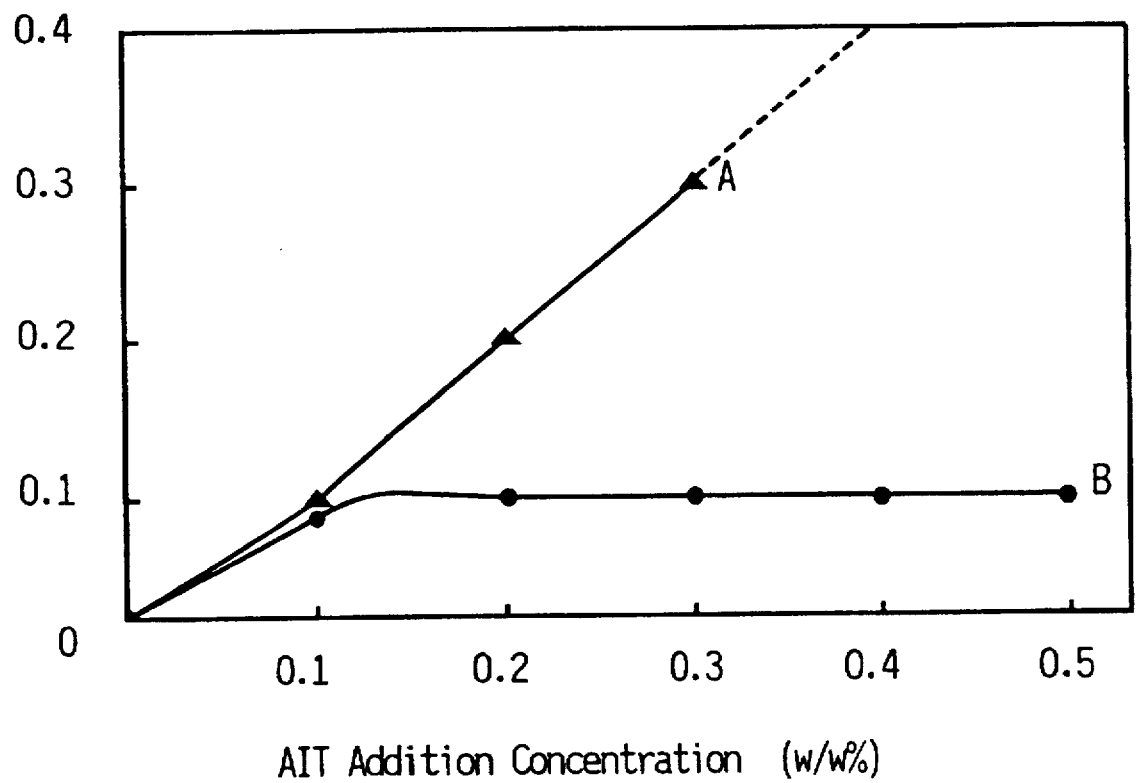

COMPOSITION CONTAINING ALLYL ISOTHIOCYANATE AND ITS USE

This is a continuation of application Ser. No. 08/022,099 filed Feb. 25, 1993 now abandoned.

FIELD OF THE INVENTION

The present invention relates to an antimicrobial composition containing allyl isothiocyanate (hereinafter abbreviated as AIT) which has antimicrobial actions such as bacteriocidal action, antibacterial action and fungicidal action. The composition is a water-soluble antimicrobial composition capable of overcoming many difficulties in handling AIT. Furthermore, the present invention provides a method for treating microorganisms or keeping freshness of perishables, which comprises treating target substances such as foods (e.g. pickled vegetables), perishables such as fruit and vegetables, and the like with the composition or an aqueous solution of said composition.

BACKGROUND OF THE INVENTION

AIT which is an ingredient of wasabi (Japanese horseradish) has been known to possess superior bacteriocidal action, antibacterial action and fungicidal action, and has been currently used as an antiseptic or a preservative in the food industry. Also, AIT is known to be highly effective in keeping freshness of perishables (Japanese Patent Unexamined Publication No. 166838/1987), and the expansion of its use is now making AIT positioned as an important and epoch-making additive useful for food hygiene.

While there are known methods for utilizing AIT which has superior actions as a bacteriocide or a freshness-keeping agent, including a method wherein such effect is achieved by bringing AIT into direct contact with food, etc., and a method wherein AIT is transpirated for use (EP-A-427862), handling of AIT is very difficult, since AIT is a highly volatile, oily liquid having a strong pungent odor. Unless many problems during use of AIT have been resolved, expansion of its application range will be less practical.

In an attempt to solve the aforementioned problems, there have been proposed many compositions containing AIT, and among them are a liquid composition wherein AIT is dissolved in an oily liquid (EP-A-427862), a solid composition wherein AIT is impregnated into a porous adsorbent and formulated into powders or granules (EP-A-427862), and a gel composition wherein AIT is encapsulated in a gel substance (EP-A-427862).

Due to the chemical properties as described, however, AIT can be used only at very low concentrations. Even when dissolution of AIT in water is desired for use, it is very difficult since AIT is an oily substance, and when AIT is dissolved at all in water as it is, its solubility is 0.1 W/W % at most, and the dissolution proceeds very slowly. In addition, AIT easily reacts with water, and gives rise to a fatal problem such that its effect can be reduced by hydrolysis during dissolution.

In view of the foregoing, the application range of AIT is deemed to be expanded greatly if AIT can be contained stably in aqueous solutions in a dissolution, dispersion, or suspension state at high concentrations. Taking the case of hypochlorous acid treatment which has been currently employed for the retention of freshness of cut vegetables, for example, hypochlorous acid is poisonous, and the vegetables treated with hypochlorous acid need to be rinsed after the treatment. On the other hand, AIT is a natural and harmless component contained in Japanese radish, cabbage, etc. Thus, the water in which AIT has been dissolved can be used safely and with ease even for foods such as vegetables for the purposes as noted above, to the extent that no rinsing is necessary. An AIT-containing composition wherein AIT is dissolved in water at a high concentration is highly useful, and has a wide variety of applicable situations. However, a water-soluble composition which permits AIT to be dissolved at a high concentration and to be stable in aqueous solutions has not been known.

SUMMARY OF THE INVENTION

An object of the present invention is to provide an AIT-containing composition which has overcome difficulties in handling AIT caused by its chemical properties, and which can be used in a diverse range of industrial fields.

Another object of the present invention is to provide an AIT-containing composition which is superior in water solubility and dissolution speed.

A still another object of the present invention is to provide a method for treating microorganisms acting on perishables, etc. by using the above-mentioned AIT-containing composition, and a method for retaining freshness of vegetables, fruits, etc. by using said composition.

In view of the various problems as described, the present inventors have conducted intensive studies with the aim of achieving the aforementioned objects, and now found that by combining AIT with a polyhydric alcohol which may have aldehyde group or ketone group, an antimicrobial composition having superior dissolution property in water, whose properties permit easy handling of AIT can be obtained. Further, they have obtained a composition with higher water solubility, enhanced dissolution speed in water, and unimpaired antimicrobial activity by adding a surfactant to the composition obtained. Such improvement in water solubility of AIT permits use of the composition, as it is or upon dissolution in a solvent such as water, for the treatment of perishables and other foods and objects for the exhibition of an antimicrobial activity and retention of freshness, which finding resulted in the completion of the invention.

Accordingly, the present invention provides a composition containing AIT and a polyhydric alcohol which may have aldehyde group or ketone group.

The present invention further provides a composition comprising a surfactant in said composition.

Also, the present invention provides a method for treating microorganisms, which comprises treating perishables, etc. with an aqueous solution containing this composition.

Further, the present invention provides a method for retaining freshness of vegetables, etc., which comprises treating them with the composition of the present invention.

BRIEF DESCRIPTION OF THE DRAWING

FIG. 1 is a graph showing solubility of an AIT-containing antimicrobial composition in water.

DETAILED DESCRIPTION OF THE INVENTION

The AIT to be used in the present invention may be natural or synthetic. For example, it may be an essential oil containing AIT, such as an extract or etude purification substance from wasabi or mustard. AIT to be used in the invention is not limited to a single active ingredient preparation containing 100% AIT, but may be any composition containing AIT. However, a natural AIT is desirable for foods. While the methods for synthesizing AIT are not subject to any particular limitation, a method comprising heating allyl iodide or allyl bromide, and sodium thiocyanate in ethanol for reaction is generally employed.

The polyhydric alcohol to be used in the present invention is an alcohol having 2 or more hydroxyl groups, preferably 2 hydroxyl groups in one molecule. Preferred examples include glycols such as propylene glycol and alginic ester of propylene glycol, and polyhydric alcohols having aldehyde group or ketone group, namely sugars, such as monosaccharides (e.g. glucose, sorbitol), disaccharides (e.g. lactose, sucrose, maltose), and polysaccharides (e.g. corn starch, chemically treated starches). Of these sugars, preferred is maltose. The preferred examples also include polyhydric alcohols having a chain structure in which carbonyl group has been reduced, and particularly preferred is mannitol.

The surfactant to be used in the present invention may be any preferably having an HLB of 1 to 20, and is optionally selected according to the purpose of use. The preferred surfactants are those having an HLB of 7 to 16. For example, glycerol fatty acid ester, sorbitan fatty acid ester, sucrose fatty acid ester, or the like may be used. The fatty acid here means those generally referred to as fatty acid, and includes those having straight chain or branched chain, which may be saturated or unsaturated.

The proportion of polyhydric alcohol to AIT in the composition of the present invention is 1–100 parts by weight, preferably 5–20 parts by weight, and more preferably 6–12 parts by weight per part by weight of AIT.

A surfactant is normally contained in the composition of the present invention in a proportion of 0.01–20, preferably 0.1–10, and more preferably 1–5 parts by weight relative to the entire part by weight of the composition as 100, and normally 0.05–1, and preferably 0.1–0.5 part by weight per part by weight of AIT in the composition.

The AIT-containing composition of the present invention can be formulated into liquids, powders, granules, tablets, or the like, with preference given to powders in view of handling.

Powdery compositions can be prepared by adding an appropriate amount of a powdery polyhydric alcohol such as maltose to AIT, or a mixture of AIT and a surfactant, and thoroughly mixing the same. Also, preparations in the form of powders, granules, tablets, or the like can be prepared by adding other suitable additives such as excipients, binders, and disintegrators.

Liquid compositions can be prepared by adding an appropriate amount of a polyhydric alcohol to AIT or a mixture of AIT and surfactant, and then dissolving same by gradually adding a solvent such as water. By varying the amounts of surfactant and solvent, solutions, emulsions, or lotions can be prepared.

The antimicrobial composition of the present invention has bacteriocidal action, bacteriostatic action, and antibacterial action on aerobic bacteria and anaerobic bacteria, as well as fungicidal action, and fungistatic action on molds, and is useful as an antimicrobial agent for various substances including foods which are subject to problems caused by growth and proliferation of deleterious microorganisms. Also, the composition of the present invention is effective in delaying deterioration of freshness of vegetables, etc., and is useful as an agent for retaining freshness.

The microorganisms to be the target for the antimicrobial action of the composition are exemplified by fungi such as blue mold, black mold and bread yeast, and bacteria such as *Staphylococcus*, *Escherichia coli* and *Salmonella typhi*.

The objects to be treated with the antimicrobial composition of the invention may be any substance that develops microorganisms, and include, for example, perishables such as leafy vegetables (e.g. cabbage, spinach), flower vegetables (e.g. broccoli), fruit vegetables (e.g. tomato, cucumber), seaweeds (e.g. *Undaria pinnatifida*), and flowering plants; processed foods such as confectioneries, side dishes, and pickles; industrial oils such as lubricating oil, and cutting oil; and household goods such as incense.

The present invention permits prevention of molding and bacterial growth by way of treatment with the composition of the invention, which in turn results in delayed rotting of perishables, etc. and prevention of excessive fermentation of foods, and the like. So as to achieve this object, the composition of the invention or water containing same only needs to be brought into contact with the treatment targets by, for example, rinsing objects such as perishables with water containing the composition, merely spraying the water onto the objects such as perishables, or adding the composition to the objects to be treated.

The concentration of AIT in an aqueous solution to be used for washing is normally 0.001–0.1 W/W %, preferably 0.005–0.05 W/W %, and more preferably 0.01–0.02 W/W %, and that in an aqueous solution to be used for spraying is normally 0.01–5 W/W %, preferably 0.1–2 W/W %, and more preferably 0.5–1 W/W %.

The method for rinsing the target objects for an antimicrobial treatment may comprise merely immersing the objects into the water containing an antimicrobial composition for 0.5–10 minutes, preferably about 5 minutes. A more preferred method comprises placing the objects in the water containing an antimicrobial composition, which is being circulated or aerated. The treatment temperature is normally low, preferably 1°–10° C.

The foods treated this way can be served as they are without rinsing.

The method comprising spraying of the water containing the antimicrobial composition onto the treatment targets is a simple and easy method which can be conducted, for example, even when goods are being displayed in a shop.

The spraying comprises, for example, charging the water containing an antimicrobial composition into a suitable sprayer, and spraying same onto the target objects.

In particular, application of the composition of the present invention to pickles, etc. can result in the prevention of molding and bacterial growth, thereby an antiseptic effect can be exerted.

As the pickles, exemplified are those pickled in salt, koji, sake lees, soy sauce, or vinegar. The composition of the present invention is added to seasoning liquids for pickling to stop fermentation at a suitable stage, thereby to obtain adequately fermented pickles. That is, excessive fermentation of pickles by bacteria can be suppressed, and preservation stability and desirable suppression of changes in taste, color, and smell caused by fermentation of the pickles can be attained. This is one of the embodiment modes of the microorganism treatment of the present invention.

Vegetables lightly pickled in salt, and other pickles can be made by using the seasoning liquids in which the composition of the invention is added. The composition of the invention may be added to the seasoning liquids for light pickles normally at an AIT concentration of 0.001–0.1 W/W %, preferably 0.005–0.03 W/W %, and more preferably 0.01–0.02 W/W % relative to the seasoning liquids.

When a treatment for retaining freshness of vegetables, etc. is performed using the composition of the present invention, the freshness retention effect is attributable to the ethylene-inhibitory action possessed by AIT. So as to achieve this object, a treatment similar to the antimicrobial treatment as described is conducted.

The objects to be treated with the composition of the present invention for retaining freshness include vegetables, fruits, and cut flowers. The vegetables include, for example, leafy vegetables such as cabbage, lettuce and spinach, flower vegetables such as broccoli; and fruit vegetables such as tomato and cucumber. The cut flowers include, for example, carnation, lily, rose and cattleya.

The present invention is hereinbelow detailedly described by illustrating examples, to which the invention is not limited.

EXAMPLE 1

A solid composition having the following formulation which was obtained by allowing maltose from among polyhydric alcohols having aldehyde group or ketone group, to entrap AIT

| | |
|---|---|
| Maltose | 99–70 parts by weight |
| AIT | 1–30 parts by weight |
| | 100 parts by weight |

EXAMPLE 2

A composition obtained by mixing a mixture of maltose and a polyhydric alcohol having aldehyde group or ketone group, with AIT

| | |
|---|---|
| Maltose | 69–40 parts by weight |
| Lactose | 1–30 parts by weight |
| AIT | 1–30 parts by weight |
| | 100 parts by weight |

EXAMPLE 3

A composition obtained by adding AIT to glycol

| | |
|---|---|
| Propylene glycol | 70–99 parts by weight |
| AIT | 1–30 parts by weight |
| | 100 parts by weight |

EXAMPLE 4

A composition obtained by adding AIT to a mixture of propylene glycol and another glycol

| | |
|---|---|
| Propylene glycol | 69–40 parts by weight |
| Propylene glycol alginate | 1–30 parts by weight |
| AIT | 1–30 parts by weight |
| | 100 parts by weight |

EXAMPLE 5

A composition obtained by adding a surfactant having an HLB of 1–20 to the composition obtained in Example 1

| | |
|---|---|
| Maltose | 98–70 parts by weight |
| AIT | 1–30 parts by weight |
| Glycerol fatty acid ester | 1–10 parts by weight |
| | 101 parts by weight |

EXAMPLE 6

A composition obtained by adding a surfactant having an HLB of 1–20 to the composition obtained in Example 3

| | |
|---|---|
| Propylene glycol | 98–70 parts by weight |
| AIT | 1–30 parts by weight |
| Glycerol fatty acid ester | 1–10 parts by weight |
| | 101 parts by weight |

EXAMPLE 7

A composition obtained by adding a surfactant having an HLB of 1–20 to a composition comprising AIT and mannitol

| | |
|---|---|
| Mannitol | 99–87 parts by weight |
| AIT | 1–17 parts by weight |
| Glycerol fatty acid ester | 1–3 parts by weight |
| | 105 parts by weight |

EXAMPLE 8

A composition comprising one of the compositions obtained in Examples 1, 3, 5, and 6; and fats and oils.

| | |
|---|---|
| Composition of Ex. 1, 3, 5, or 6 | 1–50 parts by weight |
| Coconut oil | 99–50 parts by weight |
| | 100 parts by weight |

The compositions described in Examples 1, 2, 5, and 7 may be dispensed to three or four sided seal packagings made of a film produced from aluminum and synthetic resin, and can be used as appropriate.

The compositions described in Examples 3, 4, and 6 may be dispensed to three or four sided seal packagings made of a film produced from aluminum and synthetic resin as mentioned above, or liquid bottles with scales thereon such as dropping bottles, and can be used as appropriate.

The composition described in Example 8 is obtained as a semi-solid, and it can be dispensed to three or four sided seal packagings, laminate tubes or aluminum tubes for divisional use of the composition, or capsules made of gelatin for casting adequate amounts of the composition.

EXAMPLE 9

Freshness retention of and antimicrobial effect on cut vegetables washed with water in which an AIT-containing antimicrobial composition has been dissolved
1. Method The composition obtained in Example 5 was added in a water tank for dissolution to give an aqueous solution containing 0.01 or 0.1% AIT (% by weight, hereinafter the same). In each of the solutions was immersed a cut cabbage for experiment (200 g) for 5 minutes. The cabbage was taken out, shook to let the water out, and stored at 10° C. at natural humidity. The cabbage was observed for the color change into brown and softening (visual observation), and for the change in smell, and compared with each other at immediately after the treatment, 3 days later, 5 days later, and 10 days later. As a control, used was a cut cabbage treated with water without AIT. The number of general bacteria was counted following the steps given below.

A sterilized phosphate buffer saline (90 ml) was added to 10 g of a sample vegetable, and a starting liquid sample was prepared by a homogenizer. Ten-fold series diluted solutions were prepared from the starting liquid sample. From each diluted solution was aseptically taken out 1 ml of a sample, which was inoculated on an agar medium to prepare a poured plate. After solidification, it was cultured at 37° C. for 24 hours, and the colonies that grew were counted. A standard agar medium (manufactured by Nissui Seiyaku, Japan) was used for general bacteria to count the number.

2. Results

The results are summarized in Table 1.

TABLE 1

Freshness retention of and antimicrobial effect on cut vegetables washed with water in which an AIT-containing antimicrobial composition has been dissolved

| AIT concentration, treated group | Just after treatment general plate count | 3 days later appearance | 3 days later general plate count | 5 days later appearance | 5 days later general plate count | 10 days later appearance |
|---|---|---|---|---|---|---|
| 0% | $1.3 \times 10^6$ | — | $1.6 \times 10^8$ | slight brown | $2.8 \times 10^8$ | brown, rotten |
| 0.01% | $2.0 \times 10^6$ | — | $1.1 \times 10^6$ | — | $8.9 \times 10^7$ | — |
| 0.1% | $5.0 \times 10^5$ | — | $4.3 \times 10^4$ | — | $3.4 \times 10^6$ | softening |

Note: — means no change

The comparison of viable cell number evidently shows antimicrobial effect of AIT, and the effect was eminent with the increasing treatment concentration. Those treated with a lower concentration AIT (0.01%) retained freshness in appearance, and showed viable cell numbers of $10$-$10^2$ order smaller than those of the control, thus showing that the AIT composition is effective in freshness retention and antimicrobial action.

EXAMPLE 10

Freshness retention of and antimicrobial effect on cut vegetables sprayed with water in which an AIT-containing antimicrobial composition has been dissolved 1. Method An aqueous solution having a final concentration of AIT of 0.01% was prepared by dissolving the composition of Example 5 (maltose:glycerol fatty acid ester (HLB 10):AIT= 88:2:10, by weight) in water. As the groups for comparison, aqueous solutions having a final AIT concentration of 0.01%, 0.02%, or 0.04% and containing no alcohol or surfactant were prepared by dissolving allyl mustard oil. The treatment conditions for each sample are summarized in Table 2.

TABLE 2

| Sample (treated group) | Agents used | AIT content (v/v %) |
|---|---|---|
| Control | none | 0 |
| Treated group 1 | allyl mustard oil | 0.01 |
| Treated group 2 | allyl mustard oil | 0.02 |
| Treated group 3 | allyl mustard oil | 0.04 |
| Treated group 4 | composition of the invention* | 0.01 |

Note *composition of the invention; maltose:glycerol fatty acid ester (HLB 10):AIT = 88:2:10 by weight Each aqueous solution was sprayed all over broccoli and seaweed. Thereafter, the broccoli and the seaweed were placed in 25 μm-thick CPP preservation bags, and stored at 4°–10° C. for 10 days, and then at room temperature for 10 days. Starting immediately after the treatment, changes in appearance (color change into brown and softening-rotting) of the vegetables and the seaweed were observed with time (day 10, day 20). As controls, used were broccoli and seaweed treated with water without AIT.

2. Results

The time-course changes in appearance of broccoli (color change) and seaweed (degree of rotting) are summarized in Table 3 and Table 4, respectively.

TABLE 3

Results in the case of broccoli

| Sample | Change in appearance (color) | | |
| | Just after treatment | 10 days later | 20 days later |
|---|---|---|---|
| Control | − | − | ++ |
| Treated group 1 | − | − | + |
| Treated group 2 | − | − | − |
| Treated group 3 | − | − | ++ |
| Treated group 4 | − | − | − |

Notes
−: No change,
+: change into yellow observed,
++: change into yellow observed in a wider area

TABLE 4

Results in the case of seaweed

| Sample | Change in appearance (rotting) | | |
| | Just after treatment | 10 days later | 20 days later |
|---|---|---|---|
| Control | − | ± | ++ |
| Treated group 1 | − | ± | ++ |
| Treated group 2 | − | − | ± |
| Treated group 3 | − | − | ± |
| Treated group 4 | − | − | ± |

Notes
−: No change,
±: slightly rotten,
++: considerably rotten

As regards the broccoli (Table 3), no change was observed during the 10 days' storage at a cool place. However, 10 more days' storage at room temperature resulted in color change into yellow in control and treated groups 1 and 3, in which the degree of the change into yellow was: treated group 1<control≈treated group 3. The treated groups 2 and 4 scarcely showed changes caused by degradation in freshness.

As regards the seaweed (Table 4), the treated groups 2–4 showed inhibition of changes which could be caused by degradation in freshness, as compared with the control, thus indicating that freshness could be retained.

EXAMPLE 11

Effect of AIT-containing antimicrobial composition on pickles

1. Method

The composition obtained in Example 5 (maltose:glycerol fatty acid ester (HLB 10):AIT=88:2:10 by weight) was added to a solution containing sodium chloride and sodium glutamate to prepare 5 kinds of aqueous solutions shown in Table 5.

TABLE 5

Composition of seasoning

| Sample | Amount of composition added (W/W %) | Formulation of seasoning (W/W %) | | |
|---|---|---|---|---|
| | | AIT content | NaCl | Sodium glutamate |
| Control | 0 | 0.0 | 2 | 0.1 |
| Treated group 5 | 0.025 | 0.0025 | 2 | 0.1 |
| Treated group 6 | 0.05 | 0.005 | 2 | 0.1 |
| Treated group 7 | 0.1 | 0.01 | 2 | 0.1 |
| Treated group 8 | 0.2 | 0.02 | 2 | 0.1 |

Cucumbers were left in a 5% aqueous solution of sodium chloride at a weight ratio of the cucumbers and the aqueous solution of 1:1 at room temperature for 5–6 hours for pre-pickling. Then, the cucumbers were taken out, and pickled in a seasoning liquid having a composition as shown in Table 6 (seasoning liquid:cucumber=1:1 w/w), and stored at 20° C. to observe the time-course changes in appearance. The results are summarized in Table 6.

TABLE 6

Time-course change of pickles in seasoning liquid

| Sample | AIT concentration in seasoning liquid (%) (measured*) | Cloudiness of seasoning liquid | | | | Appearance of cucumber |
|---|---|---|---|---|---|---|
| | | Just after treatment | 1 day later | 2 days later | 3 days later | 3 days later |
| Control | 0 | − | ± | ++ | ++ | in part brown |
| Treated gr. 5 | 0.002 | − | − | ++ | ++ | no change |
| Treated gr. 6 | 0.003 | − | − | + | ++ | no change |
| Treated gr. 7 | 0.009 | − | − | ± | + | no change |
| Treated gr. 8 | 0.026 | − | − | − | − | no change |

Notes
−: no clouding,
±: a little cloudy,
+: cloudy,
++: considerably cloudy

2. Results

The addition of AIT in a seasoning liquid resulted in freshness retention of pickles, and the effect was remarkable with the increasing AIT concentrations (0.002–0.026%).

EXAMPLE 12

Preservation of well-pickled cucumber by AIT-containing antimicrobial composition A well-pickled cucumber prepared with a reduced amount of salt was placed in a ca. 100 ml glass Schale by 20 g, and thereto was added 0, 0.1, 0.2, 0.5, or 1.0 ml of an aqueous solution of AIT at a final concentration of 0.1% which was prepared by dissolving the composition of Example 5, and each cucumber was preserved at 5°, 10°, 20°, or 30° C. The growth of eumycetes was visually observed. Table 7 shows the number of days needed for eumycetes to grow during the 25 day period from the initiation of the preservation. In the Table, - means no growth of eumycetes.

TABLE 7

Days up to growth of eumycetes

| AIT solution added (ml) | days passed (days) | | | |
|---|---|---|---|---|
| | 30° C. | 20° C. | 10° C. | 5° C. |
| 0 | 7 | 7 | 13 | 17 |
| 0.1 | 15 | 11 | — | — |
| 0.2 | — | 18 | — | — |
| 0.5 | — | — | — | — |
| 1.0 | — | — | — | — |

Experimental Example 1

Water solubility of AIT-containing antimicrobial composition

1. Test method

The composition obtained in Example 5 (maltose:glycerol fatty acid ester (HLB 10):AIT=88:2:10 by weight) was added to water for dissolution, and aqueous solutions of various AIT concentrations were prepared. Then, the solutions were centrifuged at 3000 rpm for 5 minutes, and the amount of AIT in water was quantitatively determined by HPLC. As a control, AIT liquid concentrate was dissolved in water for comparison.

2. Results

It was found that AIT alone could be dissolved in water only up to about 0.1 W/W %, and excess AIT separated and floated. The composition of Example 5 containing 1–10% glycerol fatty acid ester showed an increase in water solubility which was in proportion to the amount added of the glycerol fatty acid ester at least up to the solubility of 0.3 W/W %, thus permitting homogeneous and stable dissolution of AIT in water. The results are shown in FIG. 1.

Experimental Example 2

Dissolution speed of AIT-containing antimicrobial composition in water

1. Test material a) Composition of the invention maltose:glycerol fatty acid ester (HLB 10):AIT=88:2:10 b) Guaranteed AIT reagent on the market

2. Test method

To water charged in a 30 L acrylic water tank was added each test material such that the AIT concentration becomes 0.1 W/W %, and the time necessary to give a homogeneous solution was measured by visual observation while stirring. The results are shown in Table 8.

3. Results

TABLE 8

| | Immediately after | 5 min later | 10 min later | 15 min later | 20 min later | 30 min later |
|---|---|---|---|---|---|---|
| AIT reagent | oil drops (large) | oil drops (small) | oil drops (small) | oil drops (small) | oil drops (small) | homogenize |
| Composition of invention | powder* | homogenize | homogenize | homogenize | homogenize | homogenize |

While the composition of the present invention showed sedimentation of the composition powder just after the addition into the water tank (* in Table), it suspended throughout the tank upon stirring, and was homogeneously dissolved in 5 minutes.

In the case of the control AIT reagent, deposited AIT oil drops caused corrosion of the acrylic water tank. In contrast, the composition of the present invention did not cause corrosion, since the composition was quickly dissolved in water.

As described in the foregoing, the difficulty in handling AIT has been overcome by a composition containing AIT and a polyhydric alcohol which may have aldehyde group or ketone group, and the application range of AIT has been advantageously enlarged. Further, the addition of a surfactant to the composition could still enhance dissolution rate and solubility in water, thus also resulting in a divergence of use as a water-soluble composition.

The method for treating microorganisms or retaining freshness using the composition of the present invention is one example of various uses of the composition of the present invention, and the method can be applied to perishables, etc. easily and beneficially for exerting effects of antimicrobial action and freshness retention during, for example, the distribution stages from the shipment of perishables, etc. to the hands of consumers.

What is claimed:

1. A water-soluble antimicrobial composition in the form of a liquid, a powder, a granule or a tablet, comprising 1 part by weight of allyl isothiocyanate, 1–100 parts by weight of a polyhydric alcohol optionally having an aldehyde group or a ketone group, and 0.05–1 part by weight of a surfactant having an HLB of 1–20 and comprising a glycerol, sorbitan or sucrose fatty acid ester.

2. The antimicrobial composition of claim 1 in the form of a liquid.

3. The antimicrobial composition of claim 1 in the form of a powder.

4. The antimicrobial composition of claim 1 in the form of a granule.

5. The antimicrobial composition of claim 1 in the form of a tablet.

6. The antimicrobial composition of claim 1, wherein the polyhydric alcohol is a sugar.

7. The antimicrobial composition of claim 6, wherein the sugar is a monosaccharide, a disaccharide or a polysaccharide.

8. The antimicrobial composition of claim 7, wherein the sugar is selected from the group consisting of glucose, sorbitol, lactose, sucrose, maltose, and a starch.

9. The antimicrobial composition of claim 1, wherein the polyhydric alcohol is a disaccharide.

10. The antimicrobial composition of claim 9, wherein the disaccharide is maltose.

11. The antimicrobial composition of claim 1, wherein the polyhydric alcohol is mannitol.

12. The antimicrobial composition of claim 1, wherein the surfactant has an HLB of 7–16.

13. The antimicrobial composition of claim 1, wherein the surfactant is selected from the group consisting of glycerol fatty acid ester sorbitan fatty acid ester, and sucrose fatty acid ester.

14. A method for treating microorganisms, comprising washing a target substance with water containing an effective amount of the composition of claim 1, wherein the allyl isothiocyanate concentration in the water is 0.001–0.1 w/w %.

15. The method for treating microorganisms, comprising spraying water containing an effective amount of the composition of claim 1 onto a target substance, said water containing the allyl isothiocyanate in a proportion of 0.001–0.1 w/w %.

16. The method for treating microorganisms, comprising adding the composition of claim 1 or water containing an effective amount of the composition of claim 1 to a target substance, said target substance containing the allyl isothiocyanate in a proportion of 0.001–0.1 w/w %.

17. The method for treating microorganisms according to claim 14, wherein the target substance to be treated is perishables or pickles.

18. The method for treating microorganisms according to claim 15, wherein the target substance to be treated is perishables or pickles.

19. The method for treating microorganisms according to claim 16, where in the target substance to be treated is processed foods.

20. The method for treating microorganisms according to claim 16, wherein the target substance to be treated is a seasoning liquid, salt, koji, or sake lees, with which pickles are made.

21. A method for retaining the freshness of vegetables, fruits or cut flowers, comprising washing them with water containing an effective amount of the composition claim 1, said water containing the allyl isothiocyanate in a proportion of 0.001–0.1 w/w %.

22. The method for retaining freshness of vegetables, fruits or cut flowers, comprising spraying water containing an effective amount of the composition of claim 1 onto them, said water containing the allyl isothiocyanate in a proportion of 0.001–0.1 w/w %.

23. A method for forming a water-soluble solution of allyl isothiocyanate which comprises forming a water-soluble antimicrobial composition in the form of a liquid, a powder, a granule or a tablet, comprising 1 part by weight of allyl isothiocyanate, 1–100 parts by weight of a polyhydric alcohol optionally having an aldehyde group or a ketone group, and 0.05–1 part by weight of a surfactant having an HLB of 1–20 and comprising a glycerol, sorbitan or sucrose fatty acid ester; and adding the antimicrobial composition in the form of a liquid, a powder, a granule or a tablet to water in an amount sufficient to provide an antimicrobially effective amount of the allyl isothiocyanate.

* * * * *